United States Patent [19]

Corey et al.

[11] Patent Number: 4,543,421

[45] Date of Patent: Sep. 24, 1985

[54] CONJUGATE ADDITION OF ORGANOCUPRATES GENERATED FROM COPPER (I) CYANIDE AND VINYL STANNANES USEFUL IN PROSTAGLANDIN ANALOG SYNTHESIS

[75] Inventors: Paul F. Corey, Elkhart; Harold C. Kluender, South Bend, both of Ind.

[73] Assignee: Miles Laboratories, Inc., Elkhart, Ind.

[21] Appl. No.: 493,709

[22] Filed: May 11, 1983

[51] Int. Cl.$^4$ ............................................. C07C 177/00
[52] U.S. Cl. ................................. 560/106; 556/437; 560/107; 560/118; 560/121; 560/231; 562/500; 562/503; 568/379
[58] Field of Search ............... 560/121, 106, 107, 118, 560/231; 562/503, 500; 568/379; 556/437

[56] References Cited

U.S. PATENT DOCUMENTS

| | | | |
|---|---|---|---|
| 4,100,353 | 7/1978 | Buckler | 560/55 |
| 4,127,612 | 11/1978 | Kluender | 568/379 |
| 4,170,709 | 10/1979 | Kao | 560/121 |
| 4,171,331 | 10/1979 | Biddlecom | 260/946 |
| 4,363,817 | 12/1982 | Biddlecom | 424/311 |

OTHER PUBLICATIONS

E. J. Corey, et al., *J. Am. Chem. Soc.*, 94, 7210, (1972).
P. W. Collins, et al., *J. Med. Chem.*, 20, 1152, (1977).
H. C. Kluender, et al., Chemistry, Biochemistry and Pharmacological Activity of Prostanoids, p. 370.
Lipshultz, et al., *J. Am. Chem. Soc.*, 103, 7672, (1982).
Alverez, et al., *J. Am. Chem. Soc.*, 94, 7823, (1972).
Gorlier, et al., *J. C. S. Chem. Comm.*, 88, (1973).
Mandeville, et al., *J. Org. Chem.*, 39, 400, (1974).
Acker, *Tet. Letters*, 3407, (1977).
Marino, et al., *J. Org. Chem.*, 46, 4389, (1981).
House, et al., *J. Org. Chem.*, 31, 3128, (1966).
Lipshutz, *Tet. Letters*, 3755, (1982).
Posner et al., JACS 101 934, (1979).

*Primary Examiner*—Robert Gerstl
*Attorney, Agent, or Firm*—Jerome L. Jeffers

[57] ABSTRACT

An improved method for the preparation of prostaglandin analogs which comprises preparation of two equivalents of an alkyl or alkenyl lithium reagent in an aprotic solvent mixture such as pentane or hexane and tetrahydrofuran, conversion of said reagent by addition of 1 equivalent of copper (I) cyanide to a copper reagent, conversion of said copper reagent to the blocked prostaglandin analog by the addition of a 2-alkylcyclopent-2-en-1-one reagent and quenching of the resultant reaction mixture with aprotic media or an active acylating agent and finally optionally deblocking the resultant product is disclosed. This method is an improvement over previous methods in that more modest temperatures and less hazardous and/or less complex reagents are used and in that for some analogs the method is shorter than previous methods.

10 Claims, No Drawings

CONJUGATE ADDITION OF ORGANOCUPRATES GENERATED FROM COPPER (I) CYANIDE AND VINYL STANNANES USEFUL IN PROSTAGLANDIN ANALOG SYNTHESIS

BACKGROUND OF THE INVENTION

E. J. Corey, et al disclose a conjugate addition reaction in *J. Am. Chem. Soc.*, 94, 7210 (1972), which has been used by Paul W. Collins, et al, *J. Med. Chem.*, 20, 1152 (1977), and H. C. Kluender, et al, Chemistry, Biochemistry and Pharmacological Activity of Prostanoids, S. M. Roberts and F. Scheinman (eds.), page 370, Pergamon Press, Oxford and New York (1979) for the synthesis of certain prostaglandins. This method, which involves the preparation of copper (I) pentyne, its solubilization in ether with hexamethylphosphoroustriamide, the reaction of the resultant solution with an alkyl lithium at −60° C. to −78° and finally, the addition of a substituted cyclopent-2-en-1-one also at very low temperatures is suitable for bench scale preparations, however, it requires certain reagents and conditions which are undesirable in commercial scale production. These include the use of copper (I) pentyne solubilized with hexamethylphosphoroustriamide (HMPA), ethyl ether (Et$_2$O) and very low temperatures (−78° C.). The Kluender reference also used highly pyrophoric tert-butyllithium for generation of the alkyl lithium reagent.

For the commercial scale production of therapeutically useful prostaglandins, alternative reagents and conditions, as well as a reduction in the number of steps involved in product synthesis, would be desirable.

SUMMARY OF THE INVENTION

The present invention is a method for the preparation of a prostaglandin analog characterized by the formula:

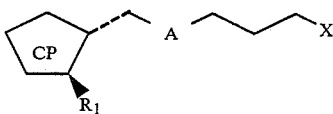

wherein

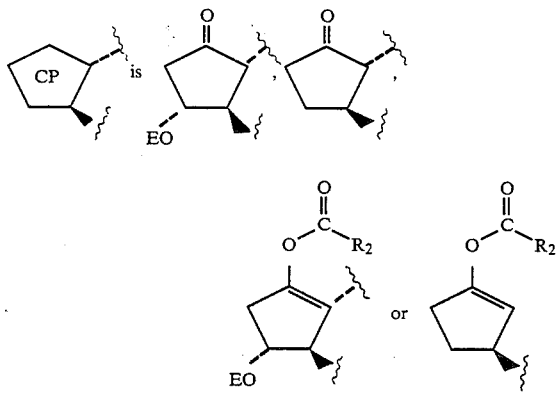

A is ethylene or cis-vinylene; X is CH$_2$OE or CO$_2$R$_3$ where E is H or an acid labile blocking group, R$_2$ is straight or branched chain lower alkyl of 1 to 4 carbon atoms or phenyl and R$_3$ is alkyl of 1 to 3 carbon atoms and R$_1$ is butyl or

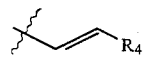

where R$_4$ is hexyl or

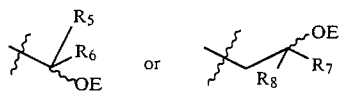

where R$_5$ is methyl or H, R$_6$ is alkyl, branched alkyl or cycloalkyl of 5 to 7 carbon atoms, R$_7$ is methyl, vinyl or H and R$_8$ is n-alkyl, branched alkyl or alkylated cycloalkyl of 4 to 7 carbon atoms which process comprises the steps of:

(a) reacting 2 equivalents of R$_1$Li wherein R$_1$ is as defined above with E being an acid labile blocking group with 1 equivalent of CuCN in an aprotic solvent under an inert atmosphere at a temperature of from −78° C. to 25° C. to form a reaction product;

(b) reacting the reaction product formed in step (a) with 1 equivalent of a substituted cyclopentenone of the structure:

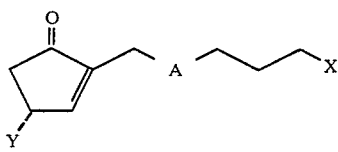

where Y is H or OE, A is as defined above and X is as defined above where E at each occurance is an acid labile blocking group to form a reaction product;

(c) quenching with an aqueous solvent or an acylating agent of the formula:

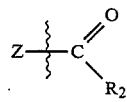

where Z is Cl, Br or

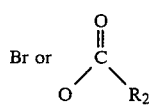

and R$_2$ is as defined above;
and (d) optionally hydrolyzing the product of step (c) with dilute acid to remove the acid labile blocking groups and form the above-described product where E is H.

DETAILED DESCRIPTION

In a preferred embodiment, compounds are prepared by the process of the present invention in which R$_2$ is phenyl, R$_3$ is methyl, R$_1$ is or butyl, R$_4$ is

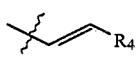

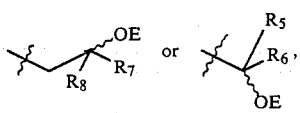

R$_5$ is H, R$_6$ is pentyl, R$_7$ is methyl, R$_8$ is butyl, A is ethylene and E is H, 1-ethoxyethyl or trimethylsilyl. The process which constitutes the present invention involves the use of a cuprate reagent of the general formula {LiCu(R$_1$)$_2$} where R$_1$ is as previously defined generated from 1 equivalent of CuCN and 2 equivalents of an alkyl or vinyl lithium in THF or THF/alkane reacts under mild conditions with appropriately functionalized cyclopentenones to afford prostagladin analogs in high yield via a conjugate addition reaction. The vinyl lithium species is generated from the corresponding vinyl stannane by action of one equivalent of n-butyllithium or from the vinyl iodide.

By using CuCN, in lieu of the prior art copper pentyne, no solubilizing agent is needed and 1 reaction step is saved since copper pentyne must be specially prepared whereas CuCN is commercially available. Also, by generating the vinyl lithium directly from a vinyl stannane, 1 reaction step is saved. The lithiation could be effected with n-butyllithium so the tert-butyllithium used in the Kluender prior art reaction is not needed. The organocuprate reagent generated in the present reaction is reactive in the presence of THF and stable at $-20°$ C. to $0°$ C. so very low temperatures and Et$_2$O can be avoided while not affecting product yield.

This invention differs from the prior art mainly in the use of CuCN as the source of copper in the organocuprate reagent used. Copper pentyne, perhaps the reagent of choice in small scale cuprate additions, has been the most utilized copper source in laboratory preparations. It is insoluble in ethereal solvents and hence must be solubilized with HMPA or some other complexing agent. Simple copper salts, such as CuBr or CuI, are well-known precursors of organocuprate reagents used in conjugate addition reactions. They are employed with or without solubilizing agents such as sulfides, amines or phosphines. Both are photosensitive, with CuBr being especially so. In one sense, CuCN is analogous to CuBr or CuI. Reaction of any of these with 2 equivalents of an alkyl lithium (RLi) yields a homocuprate of the form LiCuR$_2$.LiX(X=Br, I, CN), although the exact structure of these organocuprates is unknown. It is thus surprising that the value of CuCN in this type of chemistry has only recently come to light. Lipshultz, et al discuss reagents of the type LiCuR.LiCN where R is alkyl and their use in coupling reactions with alkyl halides in J. Am. Chem. Soc., 103, 7672 (1981). They do not use this reagent in conjugate addition reactions nor do they demonstrate formation of analogous cuprates where R is a vinyl group. A closely related cuprate reagent, known in the literature as a "cyano-cuprate", is prepared from CuCN and 1 equivalent of an alkyl lithium (RLi) to give a reagent of the form LiCu(R)CN. These reagents have been known for some time. Alverez, et al describe the preparation of such a complexed cyano-cuprate from bis(trimethylphosphite)-copper(I)cyanide and vinyl lithium with subsequent use of the reagent in a conjugate addition reaction with an α,β-unsaturated cyclopentenone as part of a prostaglandin synthesis in J. Am. Chem. Soc., 94, 7823 (1972). All other literature examples do not use such a "complexed" form of CuCN. Gorlier, et al report the reaction of CuCN with RLi(R=Me, Bu) and the use of the resulting cyano-cuprate to conjugate add to the cyclohexenone in J. C. S. Chem. Comm., 88 (1973). Mandeville, et al report the generation of a similar cyano-cuprate (R=Bu) in J. Org. Chem., 39, 400 (1974) but found that it underwent 1,4-addition to mesityl oxide in only 8% yield.

Acker reports in Tert. Letters, 3407 (1977) that simple cyano-cuprates reacted well with epoxides to give ring-open products whereas Marino and his group formed that they react well with α,β-unsaturated epoxides and with acid chlorides which is reported, inter alia, in J. Org. Chem., 46, 4389 (1981). In our hands, however, a cyano-cuprate reagent generated from CuCN and a substituted vinyl lithium did not undergo conjugate addition to the substituted cyclopentenone synthon in spite of numerous attempts.

A second difference between the presently claimed process and the prior art centers upon solvent and temperature. Reactions are typically run in Et$_2$O at a low ($-78°$ C.) temperature. For reasons of safety, it is preferable to employ THF in lieu of Et$_2$O, although it has been reported by House, et al in J. Org. Chem., 31, 3128 (1966) that THF seems to increase the amount of 1,2-addition and makes 1,4-addition "too sluggish to be practical". In the process of this invention, THF works as well as Et$_2$O giving yields equivalent to or better than those obtained using Et$_2$O. Furthermore, we have been able to perform the reaction with temperatures as high as $0°$ C. rather than requiring the very low temperatures commonly encountered in prior art reactions and ambient reaction temperatures are operable.

In the present process, a cuprate reagent of the general formula {LiCu(R$_1$)$_2$} or {LiCu(R$_1$)$_2$.LiCN} generated from 1 equivalent of CuCN and 2 equivalents of an alkyl vinyl lithium in THF or THF/alkane reacts under mild conditions with appropriately functionalized cyclopentenones to afford prostaglandin analogs in high yield via a conjugate addition reaction. The vinyl lithium species is generated from the corresponding vinyl stannane by action of 1 equivalent of n-butyllithium of from the vinyl iodide.

The prior art process reported by E. J. Corey, et al referred to previously uses an analogously reactive cuprate reagent of the form {LiCu(1-pentyne)(3-tert-butyldimethylsilyloct-1E-ene-1-yl R).LiI} prepared from 1 equivalent of copper pentyne, solubilized with HMPA, and 1 equivalent of a vinyl lithium in Et$_2$O at low temperatures. The vinyl lithium is generated from the corresponding vinyl iodide by action of 2 equivalents of tert-butyllithium. This process has several problems or difficiences such as:

(i) copper pentyne must be prepared in a 1-step process; it is unstable to air oxidation, difficult to purify and insoluble in ethereal solvents without a solubilizing agent.
(ii) HMPA is expensive and hygroscopic. Other known solubilizing agents are equally undesirable.
(iii) the use of Et$_2$O in production is extremely hazardous.

(iv) the use of t-butyllithium in production is extremely hazardous.

(v) very low temperatures (−78° C.) are not easily dealt with in production.

(vi) the vinyl iodide is prepared from the vinyl stannane in a 1-step process.

(vii) lithiation of the vinyl iodide cannot be followed by tlc because the vinyl iodide and hydrolyzed vinyl lithium compounds have similar chromatographic behavior.

The process of this invention, which simplifies the previous process and eliminates its problems has the following advantages:

(i) CuCN is cheap, stable and commercially available.

(ii) no solubilizing agent is required.

(iii) THF or THF/alkane mixtures are acceptable solvents.

(iv) The vinyl stannane is a suitable precursor for the vinyl lithium species. It is readily metalated with one equivalent of n-butyllithium at 0° C. and the completeness of the lithiation can be determined by tlc.

(v) moderate temperatures (−78° C. to ambient, preferably −40° C. to 0° C.) are suitable.

The foregoing features of the presently claimed process result in the saving of 3 synthetic steps, i.e. the preparation of copper pentyne, the conversion of the vinyl stannane to the iodide and the solubilization of the copper salt. Furthermore, less hazardous reagents are used, i.e. THF and n-butyllithium in lieu of ether and t-butyllithium and more acceptable production temperatures are suitable. The new process is less expensive then that previously used because of the relatively low cost of CuCN, the elimination of the need for expensive HMPA and the general streamlining of the process.

The preparations of reagents used for the examples of this invention are carried out as shown in Schemes I and II. Most of these reagent preparations are straightforward to one skilled in the prostaglandin art.

Thus, either I or V are prepared, blocked as either ethoxyethyl ether or trimethylsilyl ether and then reacted with tributyltinhydride and a catalytic amount of 2,2'-azobis(2-methyl-propionitrile) (AIBN) at elevated temperatures to form the vinyl stannanes IV, VII or XX by the schemes I-ii, I-iii or I-v. The preparation of the starting materials and their conversions to trialkylsilane blocked vinyl iodides is recorded for example by Sow-Mei L. Chen, et al, *J. Org. Chem.*, 43, 3450 (1978) and also by the P. W. Collins reference cited earlier.

The reaction of I with tributyltinhydride and AIBN at elevated temperatures to yield II without hydroxyl blocking is not at all obvious. A priori one might expect significant hydrogen gas evolution with proton extraction from I and little of the indicated reaction as hydrolysis would give I unchanged or as the tributylstannyl ether. II can then be used directly for the implementation of this invention, or converted to the iodovinyl compound XVII as shown in formula I-iv. The blocking of XVII with ethylvinyl ether to form XVIII is straightforward.

In all cases, the vinyl stannanes or vinyl iodides were contaminated with 10% to 20% of the cis isomers.

The preparation of cyclopentenones VIII and X and their blocking as shown in Scheme II-i and II-ii are reported in the Kluender reference earlier cited and in references cited therein. The preparation of TMS blocked XII is a straightforward extension of the methods used by the earlier cited Sow-Mei L. Chen reference to block the acid form of X as its bis TMS ether.

The examples of this invention are shown in Scheme III. In 11 cases, either a tributylstannyl vinyl or an iodovinyl compound is lithiated in tetrahydrofuran with an appropriate amount of n-butyllithium reagent and then is converted to an active copper reagent by addition of an appropriate amount of copper (I) cyanide as a dry powder. An appropriate amount of blocked cyclopentenone IX, XI or XXI is then added, and then the product of this reaction is optionally deblocked by treatment with aqueous acid.

In the cases with blocked tributylstannyl vinyl compounds IV, VII or XX, at least one equivalent of n-butyllithium reagent is needed for each equivalent of stannyl compound. This 1:1 ratio, or a slight excess of n-butyllithium, was used for examples 2a, 2d, 2f, 2g and 2i. Example 2b illustrates the consequence of using a 2:1 ratio of n-butyllithium to stannyl compound. In this case, substantial side product XIII resulting from addition of excess n-butyl reagent to the cyclopentenone is formed along with the desired prostaglandin XII. Example 2d illustrates the utility of unblocked tributylstannyl vinyl compounds such as II for this invention. In this case, one equivalent of n-butyllithium is used to react with the free hydroxyl before lithiation of the tin site takes place. Hence, two equivalents of n-butyllithium are needed for each equivalent of tributylstannyl compound. The product of the reaction after step 3 has no blocking group or one hydroxyl, but after aqueous acid treatment, the final product is the same as that obtained in the simplest case 2a. Example 2h illustrates the use of an iodovinyl compound. In this modification, a second equivalent of n-butyllithium is needed to react with the side product n-butyliodide with forms from reaction of XVIII and the first equivalent of n-butyllithium. Actually, a third equivalent was used and, consequently, significant XIII formed as was true in example 2b when excess n-butyllithium was present.

Ideally, two or more equivalents of alkenyl lithium reagent must be present when the copper (I) cyanide is added. Example 2c illustrates the effect of using a 1:1 mole ratio of copper (I) cyanide to alkenyl lithium intermediate. The 1:1 complex does not react with cyclopentenone which is recovered intact except for some degradation. In examples 2b and 2h the second equivalent of lithium reagent is excess n-butyllithium which leads to significant prostaglandin; along with the side butylated product as indicated earlier.

In all cases, the amount of cyclopentenone IX, XI or XXI used is less than or equal to ½ the total amount of active lithium reagent present before the copper addition. The percent yield of desired prostaglandin is based on the amount of cyclopentenone as the limiting reagent. In general, the cyclopentenone reagent is the most precious compound used for such a prostaglandin synthesis. The yield of 76% reported for optimized example 2i represents a very good yield of final product. Literature references such as those earlier cited typically report yields of 50% or less from such conjugate addition reactions leading to complex prostaglandins.

$\Delta^{8,9}$ enol acylate prostaglandins have been formed as useful analogs by the quench of a conjugate addition reactions with an active acyl compound such as benzoyl chloride, acetic anhydride, etc. See W. G. Biddlecom, U.S. Pat. No. 4,363,817. Example 2g of this application illustrates the utility of copper (I) cyanide derived intermediates for the production of such enol acylate analogs. In this case, benzoyl chloride is used and the enol benzoate is obtained. Any example of the Biddlecome reference could be prepared by using the appropriate vinyl lithium, the appropriate cyclopentenone and the appropriate active acyl compound.

The final acid hydrolysis step is optionally used if the desired final product is the unblocked material or omitted if the blocked material is desired.

SCHEME II (2) Examples of invention or process

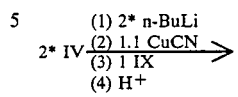

(a)

SCHEME I (1) Preparation of reagents

Vinyl stannanes

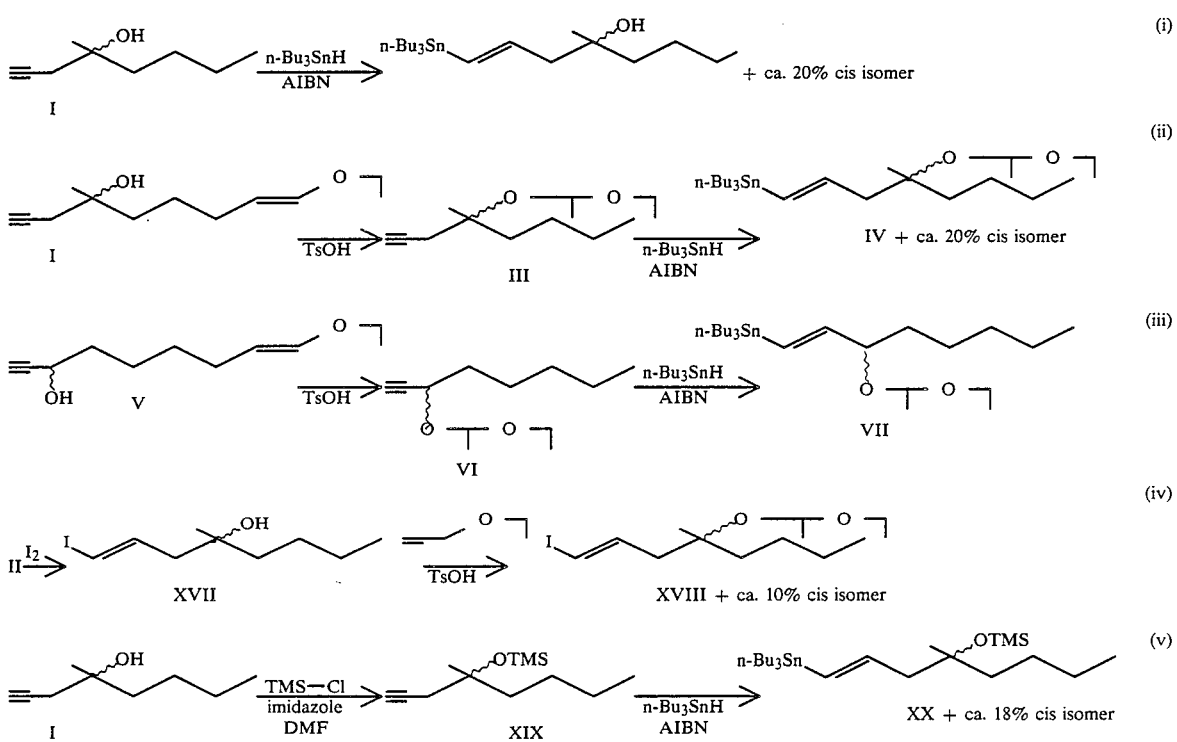

Cyclopentenones

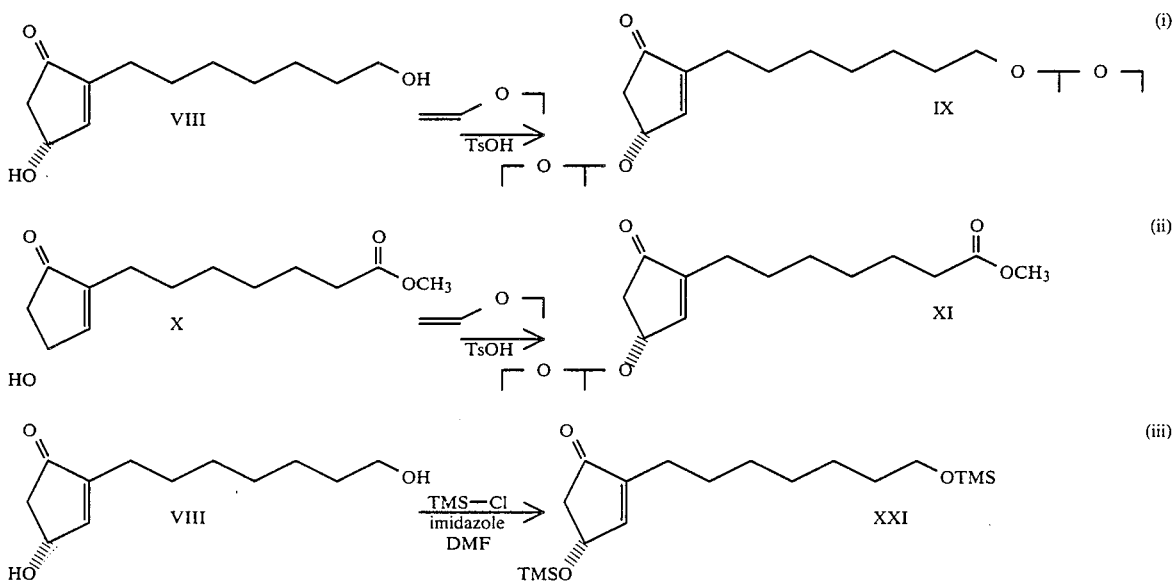

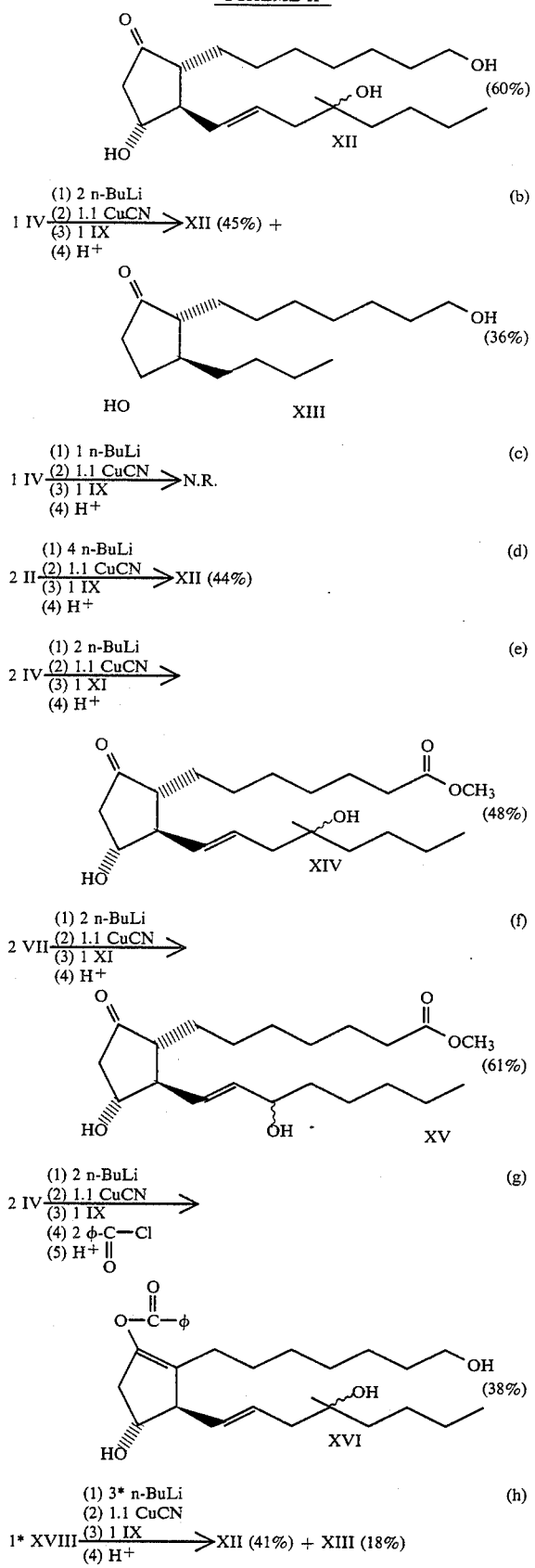

-continued
SCHEME II (i)

$2 \text{ XX} \xrightarrow[\substack{(1)\ 2\ \text{n-BuLi} \\ (2)\ 1.0\ \text{CuCN} \\ (3)\ 0.85\ \text{XXI} \\ (4)\ 0.2\ \text{n-BuLi} \\ (5)\ \text{H}^+}]{} \text{XII (76\%)}$

*Arabic numerals not in parentheses represent equivalents of reagent used.

The method of practicing the present invention is further illustrated by the following examples where the numeration corresponds with the foregoing schemes.

EXAMPLE I

Preparation of Vinyl Stannanes (a) General—the preparation of vinyl stannanes from the corresponding acetylenes and their lithiation by alkyl lithiums is known in the literature as reported by Seyferth, et al, *J. Am. Chem. Soc.*, 83, 3584 (1961) and has been used in prostaglandin synthesis as reported by Collins, et al in *Tet. Letters*, 3187 (1978).

(b) Specific vinyl stannanes

II. Compound I prepared as described by H. C. Kluender, et al in U.S. Pat. No. 4,132,738, 14.4 g (120.9 mmole) and 33 g (n-Bu)$_3$SnH (113.1 mmole) and 114 mg azobisisobutyronitrile (AIBN) was heated in a 80° C. bath under an inert atmosphere for 23 hrs., then cooled. High vacuum (ca. 1 torr) distillation affords II as a water-white liquid with bp=156°–168° C. HPLC analysis reveals contamination with ca. 20% of cis isomer; ir (thin film) cm$^{-1}$ 3350 (OH), 2940, 2910, 1458, 1370, 1060, 985; nmr (CDCl$_3$) δ 0.89 (br.t, J=7, 12H), 1.16 (s, 3H), 1.08–1.72 (m, 25H), 2.25–2.42 (m, 2H), 6.0–6.15 (m, 2H).

Anal. Calcd. for $C_{21}H_{44}OSn$: C, 58.48; H, 10.28. Found: C, 58.55; H, 10.31.

IV. A solution of 12.18 g I (86.7 mmole) and 15 ml distilled ethyl vinyl ether (157 mmole) was maintained under an inert atmosphere, cooled in an ice bath and treated with a catalytic amount of p-toluenesulfonic acid monohydrate. Formation of III was followed by tlc (silica gel plates eluted with EtOAc/Hexane (1:4); R$_f$(I)=0.28, R$_f$(III)=0.46) and took 2–5 hrs. Once III was fully formed, an excess of K$_2$CO$_3$ was added and stirred for ¼ hr. The mixture was then filtered through a bed of Celite, freed of solvent in vacuo and used without further purification. The crude III was mixed with 24 ml of (n-Bu)$_3$SnH (91 mmole) under an inert atmosphere, treated with 73 mg AIBN (0.5%), heated in an 80° C. bath for 17 hrs. and then cooled. The crude IV was chromatographed on an alumina (Fisher cat. No. A-540) column eluted with CH$_2$Cl$_2$/Hexane (1:9). The product band, detected by tlc, was collected and freed of solvent under reduced pressure to give IV as a colorless oil containing ca. 20% of the corresponding cis isomer: tlc R$_f$=0.23 (silica gel plates eluted with CH$_2$Cl$_2$/Hexane (1:2); ir (thin film) cm$^{-1}$ 2940, 2910, 2850, 1590, 1460, 1371, 1080, 956; nmr (CDCl$_3$) δ 0.75–1.05 (m, 18H), 1.17 (s, 3H), 1.05–1.70 (m, 24H), 2.25–2.45 (m, 2H), 3.53 (q, J=7, 2H), 4.83–5.16 (m, 1H), 5.90–6.10 (m, 2H).

Anal. Calcd. for $C_{25}H_{52}O_2Sn$: C, 59.65; H, 10.41. Found: C, 59.42; H, 10.38.

VII. A solution of 2.1 g V (16.7 mmole) and 3.2 ml of distilled ethyl vinyl ether (33.5 mmole) was maintained under an inert atmosphere, cooled in an ice bath and treated with a catalytic amount of p-toluene sulfonic acid monohydrate. Formation of VI was followed by tlc (silica gel plates eluted with CH$_2$Cl$_2$: R$_f$(V)=0.35, R$_f$(VI)=0.54) and took 2-5 hrs. Once VI was fully formed, an excess of K$_2$CO$_3$ was added and stirred for $\frac{1}{4}$ hr. The mixture was then filtered through a bed of Celite, freed of solvent in vacuo and used without purification. The crude VI was mixed with 4.6 ml of (n-Bu)$_3$SnH (17.5 mmole) under an inert atmosphere, treated with 30 mg AIBN, heated in an 80° C. bath for 15$\frac{1}{2}$ hrs. and then cooled. The crude VII was chromatographed on a 1$\frac{1}{2}$"×18$\frac{1}{2}$" alumina (Fisher A-540) column eluted with CH$_2$Cl$_2$/Hexane (1:9). The cis-free product band, detected by tlc, was collected and freed of solvent in vacuo to afford VII as a colorless oil: tlc R$_f$=0.46 (silica gel plates eluted with CH$_2$Cl$_2$); ir (thin film) cm$^{-1}$ 2940, 2920, 1455, 1372, 1124, 1080, 982, 950; nmr (CDCl$_3$) δ 0.70-1.12 (m, 18H), 1.06-1.80 (m, 26H), 3.25-4.20 (m, 3H), 4.51-4.90 (m, 1H), 5.80-6.12 (m, 2H).

Anal. Calcd. for C$_{24}$H$_{50}$O$_2$Sn: C, 58.91; H, 10.30. Found: C, 59.23; H, 10.50.

XVIII. This compound was prepared via a 2 step process from II by dissolving 850 g of crude undistilled II in 1.5 liters of dry ether. This solution was cooled in ice as 527 g of iodine was slowly added. The resultant solution was mixed with a solution of 175 g of potassium fluoride dihydrate in 800 ml of water and then filtered. The organic (upper) phase of the filtrate was washed with aqueous sodium thiosulate solution, then with brine. It was then dried over magnesium sulfate and distilled in vacuo to yield 445 g of pure XVII. A 314 g portion of this XVII in 200 ml of dry ether was stirred in an argon atmosphere with ice bath cooling as 96 ml of ethyl vinyl ether and 200 mg of toluenesulfonic acid was added. After two hours, the reaction mixture was washed with aqueous sodium bicarbonate solution and evaporated in vacuo to yield XVIII having R$_f$=0.43 (silica gel plates eluted with Et$_2$O/Hexane (9:1)). HPLC analysis shows ca. 10% of the cis isomer as a contaminent.

XX. XX was prepared via a 2 step process from I; the intermediate XIX was isolated and characterized.

XIX. A 56.0 g (400 mmole) portion of I was dissolved in 200 ml of dry dimethylformamide (DMF, dried over 4 Å molecular sieves for several days). The resultant solution was stirred with ice bath cooling under argon as 83 g (1.22 mmole) of imidazole (reagent grade) was added in 1 portion followed by dropwise addition via syringe of 76.1 ml (600 mmole) of chlorotrimethylsilane. The resultant mixture was left overnight as the ice bath melted (estimated 2 hrs.) and then warmed to ambient temperature. The resultant 2 liquid phase mixture was slowly poured into a swirling mixture of 500 g of ice and 750 ml of hexane. The resultant phases were separated and the lower aqueous phase was extracted with another portion of hexane. The combined organic extracts were dried (Na$_2$SO$_4$) and evaporated in vacuo (20 torr) on a rotoevaporator. The residue was distilled using a water aspirator (14-20 torr) and a 10 cm vacuum jacketed Vigreaux column to yield 3 fractions 2.58 g (bp up to 80° C., 3%), 10.25 g (bp 80°-83° C., 12.1%) and 67.08 g (bp 83°-84° C., 78.9%). GLC (6'×$\frac{1}{8}$"—2% SE-30 on 80/100 chrom. G, 110° C.) analysis of the crude material and distillation fractions showed the major desired product at 5.4 min. after the air peak with a contaminant shoulder just before the product peak. Under these conditions, starting material alcohol (I) showed a peak at 21.0 min. The % content of the contaminant was not changed significantly by distillation.

The spectral properties of the major distilled fraction were: ir (CHCl$_3$) cm$^{-1}$ 830, 1005, 1085, 1150, 1245, 1372, 1453, 2100 (weak), 2850, 2940, 3290: nmr (CDCl$_3$) δ 0.12 (s, 9H), 0.91 (br.t, 3H), 1.31 (s, 3H), 1.1-1.7 (m, 6H), 1.97 (t, J=2.7, 1H), 2.34 (d, J=2.7, 2H); C$^{13}$ nmr (CDCl$_3$) δ 2.536, 14.046, 23.216, 26.142, 27.378, 32.840, 41.619, 69.908, 75.436 (overlapped with CDCl$_3$ signal), 81.939; the contaminant showed additional weak signals at δ1.820, 23.216, 26.987, 31.344, 45.261.

XX. A mixture of 42.5 g (200 mmole) of XIX, 60.4 g tri-n-butyltin hydride (207.5 mmole) and 2.3 mg of 2,2'-azobis(2-methylpropionitrile) (AIBN) were heated in a flask under argon at 80° C. with stirring for 20 hr. then cooled. The resultant crude XX was distilled in vacuo (0.04 torr) through a 10 cm vacuum jacketed Vigreaux column. Three fractions were collected: 10.77 g (bp 39°-67° C.), 8.41 g (bp 67°-146° C.) and 81.61 g (bp 146°-158° C., 81.1% yield). HPLC (2 Whatman Partisil PXS5/25 columns, heptane at 0.5 ml/min., refractive index detection) was used to analyze the starting material components and the product distillation fractions. 10 μl injections of 5% (v/v) solutions in heptane were made showing the starting acetylene at 60 min., its contaminant (15-20%) at 82.5 min., tri-n-butyltin hydride at 16.0 min., desired 1E product at 28.0 min. and the undesired 1Z product at 26.8 min. The final 81.61 g fraction was a pure 82.1:17.9 mixture of 1E and 1Z products. The earlier fractions contained some of these products in a similar ratio along with excess tri-n-butyltin hydride and the contaminant of the starting material unchanged. Unfortunately, at a later date, this same HPLC assay system resulted in extensive decomposition during the assay. TLC (hexane) analysis of the 81 g fraction showed one spot at R$_f$=0.38 with no noticable separation of isomers. Although the R$_f$ of this material varied somewhat from 0.31 to 0.38 from day to day, perhaps dependent upon the activity of the plate, no decomposition spots such as are shown with the HPLC assay were detected over 2 weeks storage under argon at ambient temperature.

The spectral properties of the distilled material were: ir (CHCl$_3$) cm$^{-1}$ 830, 990, 1060, 1145, 1245, 1370, 1455, 1595 (weak), 2860, 2920, 2945; nmr (CDCl$_3$) δ 0.10 (s, 9H), 0.88 (br.t, J=5.9, 12H), 1.17 (s, 3H), 1.1-1.7 (m, 24H), 2.3 (m, 2H), 5.97 (m, 2H); C$^{13}$ nmr (CDCl$_3$) δ 2.666, 9.624, 10.339 (contam.), 13.656, 14.111, 16.843 (contam.), 17.168 (contam.), 23.346, 26.272, 27.313, 27.573, 28.483 (contam.), 28.808 (contam.), 29.263, 29,719 (contam.), 42.270, 42.660 (contam.), 49.748 (contam.), 51.244, 76.021, 129.803 (contam.), 130.517, 145.604 (contam.), 146.124. The contaminant signals came from the Z isomer. The relative integrations of the signals at 129.802 (Z) and 130.517 (E) or at 145.604 (Z) and 146.124 (E) indicate an 18-21% content of Z isomer which is very close to the 17.9% value obtained by HPLC analysis.

c. Cyclopentenones

VIII and IX. The preparation of these compounds is described in U.S. Pat. No. 4,159,998.

X. Described in C. J. Sih, et al., *J. Am. Chem. Soc.*, 97, 865 (1975).

XI. Protected as described in U.S. Pat. No. 4,159,998.

XXI. A solution of 17.0 g VIII (80 mmole) (as prepared in U.S. Pat. No. 4,132,738 in 50 ml of dry DMF (stored over 4 Å molecular sieves) was stirred with ice bath cooling as 20.4 g (300 mmole) of imidazole was added followed by dropwise addition of 32 ml of chlorotrimethylsilane over 10 min. At first, the mixture was a homogeneous liquid, but after ca. 20 min., it was noticed that the mixture had solidified. It was removed from the ice bath, allowed to nearly melt and then stirred without cooling for 1.5 hr. The resultant 2 liquid phase mixture was slowly poured into a vigorously swirled mixture of 200 g of ice and 300 ml of hexane. The resultant aqueous phase was separated and back extracted with 2-250 ml portions of hexane. The combined hexane extracts were dried over $Na_2SO_4$ overnight and then filtered and evaporated in vacuo (20 torr) on a rotovap and then placed in a higher vacuum (<1 torr) for 3 hrs. to remove residual solvent. The yield of the title compound was 27.1 g (95.1%) as a faint yellow oil.

Tlc analysis of this material in 3 solvent systems—EtOAc/hexane (1:1, $R_f$=0.48), EtOAc/hexane (1:3 with or without a tract of $NEt_3$, $R_f$=0.62) showed the major product always accompanied with a streak down to the origin. The IR spectrum of a fresh $CHCl_3$ solution of this material shows no free hydroxyl signal at 3200 to 3700 $cm^{-1}$.

Spectral properties of this material are: ir ($CHCl_3$) $cm^{-1}$ 710, 840, 900, 1075, 1250, 1350, 1705, 2840, 2920; nmr ($CDCl_3$) δ 0.106 (s, 9H), 0.177 (s, 9H), 1.1–2.7 (m, 10H), 2.0–3.0 (m, 4H), 3.56 (t, J=6.3, 2H), 4.9 (m, 1H), 7.1 (m, 1H); $C^{13}$ nmr ($CDCl_3$) δ 0.390, 0.520, 24.906, 26.207, 27.898, 29.589, 29.849, 33.165, 45.846, 63.015, 69.062, 147.880 (weak), 156.529, 205.953.

(d) Experimental procedures used in process of the present invention.

(i) A solution of 1.011 g IV (2.01 mmole) in 2 ml anhydrous THF and 2 ml pentane under an inert atmosphere was cooled in a −40° C. bath and treated with 1.4 ml of 1.55M n-butyllithium in hexane (2.2 mmole). After 5 min., the reaction was warmed to 0° C. (ice bath) and followed by tlc (silica gel plates eluted with $CH_2Cl_2$: $R_f$(IV)=0.55, vinyl product {4RS-methyl-4-(1-ethoxyethoxy)oct-1-ene} from quench of lithiated IV has $R_f$=0.40). Additional n-butyllithium may be added, if necessary, to complete lithiation, usually done in ¼ hr. Once lithation was complete, the clear solution was cooled in a −40° C. bath. This solution was treated with 98.5 mg CuCN (1.1 mmole) rinsed in which 1.5 ml THF—within 5 min. the CuCN dissolved leaving a homogeneous solution which was maintained at −40° C. for ¼ hour after CuCN addition. This solution was next treated with a pre-cooled (−40° C.) solution of 0.356 g IX (1.0 mmole) in 3 ml pentane and left to stir for 10 min.

Quench: The reaction mixture was transferred with 5 ml THF into a separatory funnel containing 25 ml of a solution of saturated aqueous $NH_4Cl$ made basic to pH=8-9 with concentrated $NH_4OH$ and was vigorously shaken until the organic layer was nearly colorless and the aqueous layer was blue. The phases were separated and the organic layer was extracted with a smaller portion of fresh $NH_4Cl.NH_4OH$. The combined aqueous layers were washed twice with 10 ml EtOAc then the combined organic layers were washed once with 10 ml brine and then freed of solvent under reduced pressure.

Hydrolysis of protecting groups: The residue was taken up in 50 ml of $HOAc/H_2O/THF$ (65:35:10) and stirred for 1-2 hours. at ambient temperature. The solution was then freed of solvent in vacuo and the residue was thrice triturated with 5-10 ml portions of pentane to remove the $(n-Bu)_4Sn$ by-product.

Purification: The crude product mixture was chromatographed on a ½"×13½" silica gel column eluted with EtOH/EtOAc (0.3:99.7). Fractions containing only XII, detected by tlc, were combined, filtered and freed of solvent in vacuo. The product was placed under high vacuum (ca. 1 torr) overnight (18 hrs.) affording 0.214 g XII (60%) as a pale yellow syrup possessing tlc mobility and nmr spectrum identical to TR-4698 prepared previously as described in U.S. Pat. No. 4,275,224: tlc $R_f$(Sys II)=0.29, "System II" is defined as the organic phase from a mixture of ethyl acetate, acetic acid, isooctane and water in a ratio of 11:2:5:10. This mixture is shaken thoroughly in a separatory funnel and then allowed to settle for several hrs., before the phases are separated and the organic phase used; nmr ($CDCl_3$) δ 0.92 (br.t, J=6, 3H), 1.18 (s, 3H), 1.08–1.80 (m, 18H), 1.80–2.95 (m, 9H), 3.65 (br.t., J=6, 2H), 4.08 (br.q, J=7, 1H), 5.28–6.00 (m, 2H).

(ii) Reaction (i) was repeated using only 1.0 mmole of IV and column chromatography in EtOAc, all other conditions being the same. XII (45%) and XIII (36%), identified by its nmr spectrum, were isolated: tlc (XIII) $R_f$(EtOAc)=0.408; nmr (XIII) ($CDCl_3$) δ 0.93 (br.t, 3H), 1.10–2.05 (m, 22H), 2.08–2.90 (q of d, 2H), 3.64 (t, J=6, 2H), 4.20 (br.q, 1H).

(iii) Reaction (i) was repeated using only 1.0 mmole IV and 1.0 mmole n-butyllithium, all other conditions being the same. No XII or XIII was isolated; a significant amount of VIII resulting from hydrolysis of IX was the only isolated product.

(iv) Reaction (i) was repeated using 2.0 mmole II in lieu of IV and 4.0 mmole of n-butyllithium; all other conditions remained the same. Tlc prior to purification revealed a significant reduction in the amount of cis-XII (which is typically present due to the ca. 15% cis-stannane) present in this reaction. XII (44%) was isolated after purification.

(v) Reaction (i) was repeated using 1.0 mmole XI in lieu of the IX and column chromatography in EtOAc, all other conditions being the same. XIV (48%), possessing tlc mobility and nmr spectrum identical to TR-4704 prepared previously as described in U.S. Pat. No. 4,275,224, was isolated after purification: nmr ($CDCl_3$) δ 0.92 (br.t, J=6, 3H), 1.18 (s, 3H), 1.05–1.80 (m, 16H), 1.80–2.95 (m, 10H), 3.66 (s, 3H), 4.05 (br.q, J=8, 1H), 5.25–5.95 (m, 2H).

(vi) Reaction (i) was repeated using 2.0 mmole VII in lieu of IV, 1.0 mmole XI in lieu of IX and column chromatography in EtOAc/Hexane (3:1), all other conditions being the same. XV (61%) was isolated in 2 chromatographically separable products consisting of 29% $PGE_1$-methyl ester and 32% epi-$PGE_1$-methyl ester. Both isomers possessed identical proton nmr spectra; the nmr spectra were the same as that reported previously for $PGE_1$-methyl ester as reported by C. J. Sih, et al, *J. Am. Chem. Soc.*, 97, 865 (1975); nmr ($CDCl_3$) δ 0.89 (br.t, J=6, 3H), 1.10–1.80 (m, 18H), 1.80–2.95 (m, 8H), 3.69 (s, 3H), 3.95–4.27 (m, 2H), 5.55–5.73 (m, 2H).

(vii) Reaction (i) was repeated, except that prior to the quench, 2.0 mmole of benzoyl chloride was added and allowed to stir for ¼ hour. After column chromatography in EtOAc/Hexane (2:1), the enol benzoate XVI (38%) was isolated as a colorless syrup: nmr ($CDCl_3$) δ 0.91 (br.t, J=7, 3H), 1.17 (s, 3H), 1.05–1.75 (m, 18H), 1.75–2.10 (m, 2H), 2.10–2.36 (d, J=6.5, 2H), 2.36–2.80 (br.s, 2H), 2.80–3.00 (m, 1H), 3.00–3.30 (m, 1H), 3.45–3.75 (m, 2H), 4.10–4.30 (m, 1H), 5.20–5.90 (m, 2H), 7.35–8.20 (m, 5H); ir ($CHCl_3$) $cm^{-1}$ 3400 (OH), 2920, 2845, 1720 (C=O), 1445, 1260, 1060, 965, 690; $[\alpha]_D = -71.4°$ C. (c=1.0, CHCl$_3$); R$_f$(System II)=0.46.

(viii) A solution of 0.343 g XVIII (1.01 mmole) in 2 ml anhydrous THF and 2 ml pentane under an inert atmosphere was cooled in a −40° C. bath and treated with 1.95 ml of 1.55M n-butyllithium (3.02 mmole) in 3 portions over 5 min. A thick white precipitate formed after the second portion was added. The mixture was allowed to stir for ¼ hr. after the third portion was added. Next, 98.5 mg CuCN (1.1 mmole) was added as a solid, allowed to stir for ¼ hr. and then treated with a pre-cooled (−40° C.) solution of 0.356 g IX (1.0 mmole) in 3 ml pentane. The reaction was stirred for 10 min., then quenched, hydrolyzed and chromatographed as per (i) except that EtOAc was used for the chromatography. XIII (41%) and XIII (18%) were isolated and identified by their nmr spectra (see (i) and (ii)).

(ix) A 70.4 g (140 mmole) portion of XX was stirred as a solution in 80 ml of dry THF under argon in a 1 L round bottom flask fitted with a magnetic stir bar, argon inlet, septum-closed side arm and low temperature thermometer in the usual way with −20° C. bath cooling. A 1.80M solution of n-butyllithium in hexane was added via a 50 ml syringe at 8.0 ml/min. using a syringe drive. A 40.0 ml portion was thus added resulting in a smooth exotherm of the reaction pot contents from −18.5° C. to −8.7° C. A 38.0 ml portion of n-butyllithium solution (total 78.0 ml, 140.4 mmole) was then added in the same way after the syringe was refilled. The total addition took ca. 13 min., 3 min. of which was a refill period, and the final internal temperature was −9° C. After another 17 min., a small sample was removed by glass capillary, spotted on a tlc plate along side of a spot of starting material (XX) and then eluted with hexane. The major product appeared at R$_f$=0.32 with some starting material showing at R$_f$=0.40 as brown spots and the side product tetrabutyltin showing as a white spot at R$_f$=0.70 after the usual visualization with ceric sulfate spray. As the tlc analysis was being run, the −20° C. bath was replaced with a 0° C. bath for 13 min. before the −20° C. (now −18° C.) bath was used again. A tlc analysis was repeated and showed very little change in the ratio of starting material to product. It is not clear that the 0° C. treatment was needed. An auger-drive solid addition funnel was used to add 6.27 g (70 mmole) of dried copper (I) cyanide over 5 min. to the reaction mixture with care taken not to drop the dry powder on the wet thermometer, as this was found to lead to a dark colored lump reaction mixture in a smaller scale trial reaction. A 6 ml portion of dry THF was used to rinse final traces of CuCN from the addition funnel into the reaction mixture. After 11 min., a 21.5 g (60.4 mmole) portion of XXI was added dropwise from a dropping funnel over 19 min. followed by 10 ml dry THF rinse. This addition resulted in an exotherm from −16° C. to −8° C. with a −17° C. bath. After another 10 min., an extra 8 ml portion (14.4 mmole) of n-butyllithium solution was added via syringe resulting in an exotherm from −13° C. to −11.5° C. The resultant solution was stirred 15 min. with cooling continued.

In a meantime, a quench mixture was prepared by adding 6.6 ml of concentrated (98%) sulfuric acid to 200 g of ice and 200 ml of hexane in a 1 L round bottom flask equipped with a magnetic stirrer. The reaction pot contents were blown under slight argon pressure through a teflon tube into the quench mixture as it was rapidly stirred with ice bath cooling. The resultant mixture was stirred vigorously and then filtered through Celite. The quench flask and Celite were rinsed down with several portions of hexane and the combined filtrate phases were separated. The organic (upper) phase was washed with 2-125 ml portions of brine then with 1 portion of 200 ml saturated aqueous NaHCO$_3$. Additional dark precipitate formed throughout these wash procedures and made phase separation difficult. The whole mixture was again filtered through Celite during the NaHCO$_3$ wash. The final dark red/orange upper organic phase was treated with 2.5 g of Nuchar C-190-N and anhydrous Na$_2$SO$_4$. This was filtered and then evaporated in vacuo (20 torr). The final yield of blocked TR-4698 was 101.7 g of an orange oil. The theoretical residue at this state is 34.4 g of blocked TR-4698 along with 17.0 g of side product-4-methyl-4RS-(trimethylsilyloxy)oct-3-ene and 48.6 g of side product tetrabutyltin or a total theoretical residue of 100.0 g. A tlc (EtOAc/hexane 1:3) analysis of the product showed the expected side products at R$_f$=0.78, a small uv-active side product of R$_f$=0.64, the desired product at R$_f$=0.72 and 3 additional non-uv active products at R$_f$=0.50, 0.39 and 0.17. It is thought that the 3 extra products are partially deblocked desired product and represent no loss in yield.

The blocked residue was stirred with 200 ml of ethanol, 100 ml of water and 5.5 ml of acetic acid for 2.3 hr. and then evaporated in vacuo (20 torr). The resultant residue was mixed with 200 ml of EtOAc and washed with 200 ml of saturated aqueous NaHCO$_3$. The wash solution was back extracted with 200 ml portions of EtOAc twice. The combined organic layers were dried (MgSO$_4$) and evaporated in vacuo (20 torr then −1 torr). The resultant 2 phase residue was triturated with hexane to remove the tetrabutyltin phase and the remaining yellow residue was pumped on (<1 torr) briefly to yield a residue of crude XII—23.5 g (theoretical 21.4 g). The crude product was purified to yield 16.3 g (76.3%) of acceptably pure TR-4698 and a small amount of impure fractions.

What is claimed is:

1. A process for the preparation of a prostaglandin analog characterized by the formula:

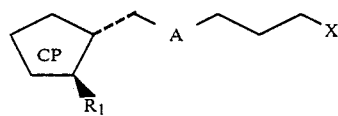

wherein

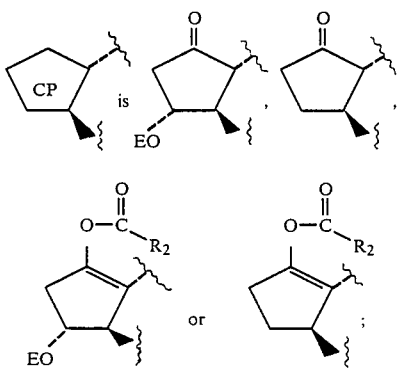

A is ethylene or cis-vinylene; X is CH₂OE or CO₂R₃ where E is H or an acid labile blocking group, R₂ is lower straight or branched chain lower alkyl of 1 to 4 carbon atoms or phenyl and R₃ is alkyl of 1 to 3 carbon atoms and R₁ is butyl or

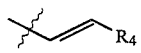

where R₄ is hexyl or

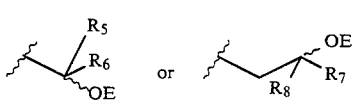

where R₅ is methyl or H, R₆ is alkyl, branched alkyl or cycloalkyl of 5 to 7 carbon atoms, R₇ is methyl, vinyl or H and R₈ is n-alkyl, branched alkyl or alkylated cycloalkyl of 4 to 7 carbon atoms which process comprises the steps of:

(a) reacting 2 equivalents of R₁Li wherein R₁ is as defined above with E being an acid labile blocking group with 1 equivalent of CuCN in an aprotic solvent under an inert atmosphere at a temperature of from −78° C. to 25° C. to form a reaction product;

(b) reacting the reaction product formed in step (a) with 1 equivalent of a substituted cyclopentenone of the structure:

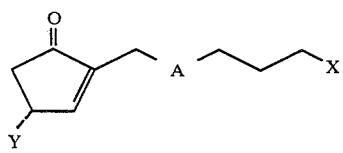

where Y is OH or OE, A is as defined above and X is as defined above where E at each occurance is an acid labile blocking group to form a reaction product;

(c) quenching with an aqueous solvent or an acylating agent of the formula:

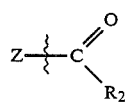

where Z is Cl, Br or

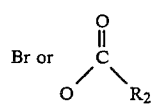

and R₂ is as defined above; and (d) optionally hydrolyzing the product of step (c) with dilute acid to remove the acid labile blocking groups and form the above-described product where E is H.

2. The method of claim 1 wherein R₂ is phenyl, R₃ is methyl, R₁ is

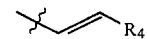

or butyl, R₄ is

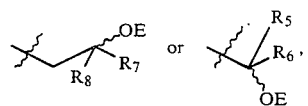

R₅ is H, R₆ is pentyl, R₇ is methyl, R₈ is butyl, A is ethylene and E is H, 1-ethoxyethyl or trimethylsilyl.

3. The method of claim 1 wherein the reaction temperature is from −40° C. to 0° C.

4. The method of claim 1 wherein

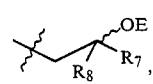

A is ethylene, X is CH₂OE where E is H, 1-ethoxyethyl or trimethylsilyl, R₁ is

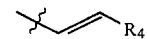

R₄ is

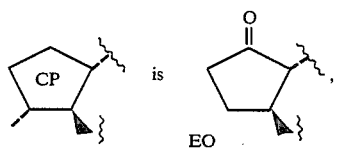

R₇ is methyl and R₈ is n-butyl.

5. The method of claim 1 wherein

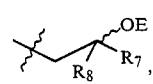

A is ethylene, X is CH₂OE where E is H or 1-ethoxyethyl and R₁ is butyl.

6. The method of claim 1 wherein

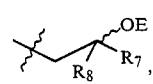

A is ethylene, X is CO₂R₃, E is 1-ethoxyethyl or H, R₁ is

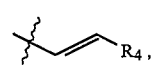

R₃ is methyl, R₄ is

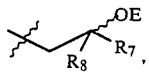

$R_7$ is methyl and $R_8$ is n-butyl.

7. The method of claim 1 wherein

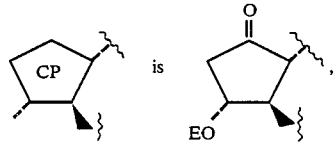

A is ethylene, X is $CO_2R_3$, E is H or 1-ethoxyethyl, $R_1$ is

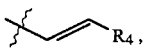

$R_3$ is methyl, $R_4$ is

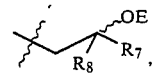

$R_5$ is H and $R_6$ is n-pentyl.

8. The method of claim 1 wherein

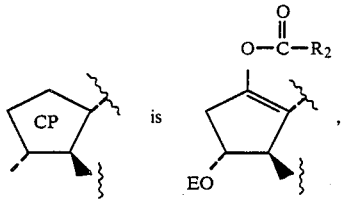

A is ethylene, E is H or 1-ethoxyethyl, X is $CH_2OE$, $R_1$ is

$R_2$ is phenyl, $R_4$ is

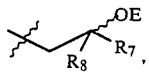

$R_7$ is methyl and $R_8$ is n-butyl.

9. The process of claim 1 wherein the aprotic solvent is a mixture of pentane and/or hexane with tetrahydrofuran.

10. The process of claim 1 wherein A is ethylene.

* * * * *

UNITED STATES PATENT AND TRADEMARK OFFICE
CERTIFICATE OF CORRECTION

PATENT NO. : 4,543,421
DATED : September 24, 1985
INVENTOR(S) : Paul F. Corey et al It is certified that error appears in the above-identified patent and that said Letters Patent are hereby corrected as shown below:

| | | |
|---|---|---|
| Column 2, line 53 | Delete "Br or". | |
| Column 4, line 14 | Change "Tert." to ---Tet.---. | |
| Column 4, line 43 | Insert ---or--- between "alkyl" and "vinyl". | |
| Column 4, line 48 | Change "of" to ---or--- third occurrence. | |
| Column 6, line 4 | Change "11" to ---all---. | |
| Column 6, line 17 | Insert ---2c--- between "2a" and "2d". | |
| Column 7, line 2 | Change "Biddlecome" to ---Biddlecom---. | |
| Column 11, line 30 | Change "314g" to ---134g---. | |
| Column 11, line 67 | Change "21.0 min." to ---2.10 min.---. | |
| Column 12, line 50 | Change "129.803" to ---129.802---. | |
| Column 15, line 49 | Change "lump" to ---lumpy---. | |
| Column 16, line 16 | Change "oct-3-ene" to ---oct-1-ene---. | |
| Column 16, line 33 | Change "20 torr then -1" to ---20 torr then <1---. | |
| Column 17, line 42 | Change "OH" to ---H---. | |
| Column 17, line 58 | Delete "Br or". | |

Signed and Sealed this

Fourteenth Day of January 1986

[SEAL]

Attest:

DONALD J. QUIGG

Attesting Officer   Commissioner of Patents and Trademarks